(12) United States Patent
Daval

(10) Patent No.: US 7,377,300 B2
(45) Date of Patent: May 27, 2008

(54) ELASTIC TIRE FOR MEASURING THE GRIP OF A VEHICLE EQUIPPED THEREWITH ON A GROUND

(75) Inventor: Bertrand Daval, Bara (JP)

(73) Assignee: Michelin Recherche Et Technique S.A., Granges-Paccot (CH)

( * ) Notice: Subject to any disclaimer, the term of this patent is extended or adjusted under 35 U.S.C. 154(b) by 325 days.

(21) Appl. No.: 10/920,550

(22) Filed: Aug. 18, 2004

(65) Prior Publication Data

US 2005/0155685 A1    Jul. 21, 2005

Related U.S. Application Data

(63) Continuation of application No. PCT/EP03/01558, filed on Feb. 17, 2003.

(30) Foreign Application Priority Data

Feb. 22, 2002    (FR) .................................. 02 02504

(51) Int. Cl.
*B60C 11/00*    (2006.01)
*B60C 11/11*    (2006.01)
*B60C 11/117*    (2006.01)
*B60C 11/12*    (2006.01)
*B60C 23/00*    (2006.01)
*G01M 17/02*    (2006.01)

(52) U.S. Cl. .................. 152/152.1; 73/146; 152/209.4; 152/209.7; 152/209.17; 152/209.18; 152/212; 152/458; 152/902; 152/DIG. 3

(58) Field of Classification Search ............. 152/152.1, 152/209.7, 209.17, 209.18, 212, 458, 902, 152/DIG. 3, 209.4; 73/146
See application file for complete search history.

(56) References Cited

U.S. PATENT DOCUMENTS 1,537,456 A * 5/1925 Brown ....................... 152/212

(Continued)

FOREIGN PATENT DOCUMENTS

DE            3937966            5/1991

(Continued)

*Primary Examiner*—Steven D. Maki
(74) *Attorney, Agent, or Firm*—Fitzpatrick, Cella, Harper & Scinto

(57) ABSTRACT

An elastic tire according to the invention comprises a tread (1) which comprises at least one unit (3) for measuring the grip of the tire on the ground, the measuring unit (3) being intended to come into contact with the ground on each revolution of the tire, and comprising, viewed at a radially outer face (5) of the tread (1), a central zone (10) and an encircling zone (20) surrounding the central zone (10), a sensor (40) sensitive to at least a tangential force exerted on the radially outer top (11) of the central zone (10) being provided opposite the top (11), the central zone (10) and the encircling zone (20) satisfying the two conditions:

a) $Rzz_c < Rzz_e$, and
b) (i) $Rxz_c/Rzz_c > Rxz_e/Rzz_e$ or (ii) $Ryz_c/Rzz_c > Ryz_e/Rzz_e$, where: x, y and z represent the circumferential, axial and radial directions for the tire, $Rzz_c$ and $Rzz_e$ represent the rigidities of the central zone (10) and of the encircling zone (20) under a force oriented perpendicularly to the radially outer face (5), $Rxz_c$ and $Rxz_e$ represent the rigidities of the central zone (10) and of the encircling zone (20) under a force oriented tangentially to the radially outer face (5) in the circumferential direction (X) of the tire, and $Ryz_c$ and $Ryz_e$ represent the rigidities of the central zone (10) and of the encircling zone (20) under a force oriented tangentially to the radially outer face (5) in the axial direction (Y).

28 Claims, 3 Drawing Sheets

U.S. PATENT DOCUMENTS

| | | | |
|---|---|---|---|
| 1,948,311 A * | 2/1934 | Orr | 152/212 |
| 4,249,588 A * | 2/1981 | Egan | 152/209.7 |
| 5,864,056 A | 1/1999 | Bell et al. | 73/146 |
| 6,666,079 B2 * | 12/2003 | Poulbot et al. | 73/146 |
| 2002/0157746 A1 | 10/2002 | Merino-Lopez et al. | 152/209.5 |

FOREIGN PATENT DOCUMENTS

| | | | |
|---|---|---|---|
| DE | 3939917 | | 6/1991 |
| DE | 19945264 | | 3/2001 |
| EP | 0937615 | | 8/1999 |
| EP | 1076235 | | 2/2001 |
| EP | 1231120 | | 8/2002 |
| EP | 1275949 | * | 1/2003 |
| FR | 2475993 | * | 8/1981 |
| JP | 62-006802 | * | 1/1987 |
| JP | 06-171321 | * | 6/1994 |

* cited by examiner

ELASTIC TIRE FOR MEASURING THE GRIP OF A VEHICLE EQUIPPED THEREWITH ON A GROUND

CROSS REFERENCE TO RELATED APPLICATIONS

This is a continuation of International Patent Application Number PCT/EP03/01558, filed on Feb. 17, 2003, which claims priority to French Patent Application Number 02/02504, filed on Feb. 22, 2002.

BACKGROUND OF THE INVENTION

1. The Field of the Invention

The present invention relates to an elastic tire, such as a pneumatic tire, provided with means permitting measurement of the grip of a vehicle equipped therewith on a surface on which the tire rolls (rolling ground), such as a roadway. It concerns more particularly the determination of grip characteristics of such an elastic tire on rolling, based on obtaining physical parameters in the contact area between this elastic tire and the rolling surface.

2. The Related Art

It has already been proposed to carry out continuous measurements in the tread of a pneumatic tire while a vehicle equipped therewith is driving, in order to know in real time the forces which develop between a pneumatic tire and the ground. The patent document DE-A-3937966 may be consulted on this subject. Nevertheless, however interesting it may be, such information is still insufficient, since the driver, or even an automatic device such as those referred to by the well-known designations in the automotive field of "ABS" or "ESP", is still incapable of anticipating a deterioration in the grip. One therefore contents oneself with noting a posteriori the exceeding of a grip limit, and as rapid action as possible is taken to control the vehicle.

There exists in this respect a need to obtain indications "in real time" of the grip conditions liable to affect, in the instants which follow, the behavior of a vehicle, notably in cases where it undergoes a substantial acceleration, due to driving or braking forces or to a change in trajectory.

SUMMARY OF THE INVENTION

The object of the present invention is to propose an elastic tire, such as a pneumatic tire, comprising a tread which comprises at least one measuring unit permitting measurement in an effective manner of the grip of the tire on a surface on which the tire rolls (rolling ground) by procuring as realistic information as possible on the safety margin which subsists in the driving of the vehicle.

To this end, an elastic tire according to the invention is such that this measuring unit, which is intended to come into contact with the ground on each revolution of the said tire, comprises, viewed at a radially outer face of the tread, a central zone and an encircling zone surrounding the central zone, a sensor sensitive to at least a tangential force exerted on the radially outer top of the said central zone being provided facing the said top, the said central zone and the said encircling zone satisfying both of the two following conditions:

a) $Rzz_c < Rzz_e$, and b) (i) $Rxz_c/Rzz_c > Rxz_e/Rzz_e$ or (ii) $Ryz_c/Rzz_c > Ryz_e/Rzz_e$, where: x, y and z respectively represent the circumferential, axial and radial directions for the said tire, $Rzz_c$ and $Rzz_e$ respectively represent the rigidities of the said central zone and of the said encircling zone under a force oriented perpendicularly to the said radially outer face, $Rxz_c$ and $Rxz_e$ respectively represent the rigidities of the said central zone and of the said encircling zone under a force oriented tangentially to the said radially outer face in the circumferential direction of the tire, and $Ryz_c$ and $Ryz_e$ respectively represent the rigidities of the said central zone and of the said encircling zone under a force oriented tangentially to the said radially outer face in the axial direction of the tire.

The aforementioned condition a) expresses the fact that the central zone has a "vertical" rigidity (i.e. in the radial direction of the tire) less than that of the encircling zone. As for the condition b), it expresses the fact that the ratio of the "tangential" rigidity (i.e. in the circumferential or axial direction of the tire) over the "vertical" rigidity is, on contrast, greater for the central zone than the encircling zone.

According to the invention, the central zone may additionally have a grip potential which is smaller than that of the encircling zone and than that of the rest of the tread. To accomplish this, this central zone may, for example, consist of a material which differs from that of the encircling zone and from the rest of the tread.

In fact, the applicant has discovered in the course of its investigations that a minimization of the "vertical" rigidity combined with a maximization of this ratio ("tangential" rigidity/"vertical" rigidity) makes it possible to create slippage of the said or each central zone by causing it to exceed the grip limit in numerous rolling circumstances, whereas the rest of the tread does not exceed this grip limit, and therefore does not slip.

If at least one suitable measurement is performed in this central zone, it is possible to arrive at a knowledge of the grip potential. Whenever the performing of a measurement is referred to here, the sensor or sensors required may be outside the tire or embedded within its mass.

Here, "measuring unit" is taken to mean a part of the tread of the tire whose structure is adapted to the aim pursued by the invention. A sensor for carrying out a measurement is implanted in this measuring unit. The adaptation consists in providing a central measurement zone surrounded by an encircling zone and having properties identical to what is used in a significant part of the tread. "Properties" is taken to mean an overall evaluation having a contribution stemming from the intrinsic characteristics of the material used, and in certain cases a contribution determined by the form given by the molding of the material, it even being possible for the latter to predominate. "Significant part" is taken to mean a part of the tread which is designed solely as a function of the use properties which the designer of the tire desired to confer on the tire in question, in contrast to what is desired in order to carry out a measurement.

Hereinbelow, "adherence potential of any element" is taken to mean the ratio between the overall maximum tangential force which this element, considered in its totality, may be subjected to during its contact with the ground at a given place, and the normal force applied to this element.

"Friction potential" designates the ratio between the local tangential stress and the local vertical stress which are exerted at a given point on a tread element slipping on the ground.

What is called "available grip margin" is the difference between the grip potential of an element and the ratio between the overall tangential force and the overall vertical force actually applied to this element, considered in its totality, during its passage through the contact area.

Preferably, the invention relates to an elastic tire consisting of a pneumatic tire whose tread is based on rubber.

According to a preferred characteristic of the invention, the tread of the elastic tire comprises tread-pattern blocks separated from one another by grooves with a width generally equal to or greater than 2 mm, the encircling zone being separated from the central zone by sipes and/or incision(s) which have a substantially smaller width than that of the said grooves and which are provided to decouple the material of the central zone from that of the encircling zone. These sipes and/or incision(s) have typically widths less than 2 mm and preferably less than 1 mm. Still more preferably, they have widths ranging from 0.3 mm to 0.8 mm.

According to another preferred characteristic of the invention, the area of the top of the central zone is less than 20% of the area of the radially outer face of the encircling zone. It will be noted that by virtue of this smaller area, the radially outer face of the central zone does not take up all of the forces exerted on the crown reinforcement of the tire upon the passage through the contact area.

Preferably, the "vertical" rigidity of the central zone is minimized to such a point that the tire according to the invention additionally satisfies the following condition:

$a^a$) $Rzz_c < 0.2 \cdot Rzz_e$.

Likewise preferably, the ratio ("tangential" rigidity/"vertical" rigidity) for the central zone is maximized to such a point that the said tire additionally satisfies the following condition:

$b^a$) (i) $Rxz_c/Rzz_c > 1.5 \cdot Rxz_e/Rzz_e$ or (ii) $Ryz_c/Rzz_c > 1.5 \cdot Ryz_e/Rzz$ These two characteristics make it possible further to optimize the development of slippage of the central zone compared with the encircling zone.

According to one embodiment of the invention, the central zone consists of a compressible isotropic material, such as a cellular rubber composition (i.e. alveolar, for example with closed cells, which is obtained in a known manner with the aid of a swelling agent), thereby helping to minimize significantly the "vertical" rigidity $Rzz_c$, of the central zone and therefore to maximize the ratio of rigidities $Rxz_c/Rzz_c$ or $Ryz_c/Rzz_c$, and hence achieve the desired optimization of the development of slippage of the said central zone.

According to another embodiment of the invention, the said central zone has an orthotropic nature, and it consists of composite layers which are superposed either in the axial direction or in the circumferential direction of the tire (respectively when the said condition b) is satisfied by the said inequality (i) or by the said inequality (ii)) and which are each based on a rubber composition in which reinforcements of organic or inorganic type, for example metal or textile reinforcements, are oriented substantially parallel to the circumferential mid-plane of the said tire or else perpendicularly to this plane (superposition of the said layers in the circumferential and axial directions, respectively).

Advantageously, the said composite layers which are in adjacent pairs respectively comprise textile fibers which are oriented at opposite angles with the circumferential or axial direction of the tire.

Preferably, these angles are substantially between ±20° and ±45° and, still more preferably, they are substantially equal to ±30°.

Each composite layer preferably has a thickness ranging from 0.5 mm to 3 mm and, still more preferably, ranging from 0.5 mm to 1 mm.

This orthotropic composite structure of the central zone makes it possible to increase the "tangential" rigidity Rxz or Ryz of this zone for a given "vertical" rigidity, thereby helping to maximize further the aforementioned ratio of rigidities $Rxz_c/Rzz_c$ or $Ryz_c/Rzz_c$ and consequently to optimize the creation of slippage in the said central zone.

It will be noted that the anisotropy ratio in extension or compression of such a composite central zone according to the invention may range from 3 to 7 and, preferably, from 3 to 4.

According to a first exemplary embodiment of the invention which may comprise any one of the above-mentioned characteristics, the said central zone substantially has the circumferential mid-plane of the said tire as element of symmetry, and the said condition b) is satisfied by the said inequality (i).

According to another characteristic of this first exemplary embodiment of the invention, the said central zone has an elongated shape (for example rectangular or ellipsoid) in the said circumferential direction of the said tire.

It will be noted that this smaller width of the central zone (in the axial direction of the tire for this first exemplary embodiment) contributes to minimize the "vertical" rigidity Rzz of the central zone and, consequently, to maximize specifically the ratio of rigidities $Rxz_c/Rzz_c$, and hence achieve the desired optimization of the development of slippage of the central zone.

According to a further characteristic of this first example, the said top of the said central zone, which is of parallelepipedal shape, has its sides respectively facing four parallelepipedal tread-pattern elements forming the said encircling zone.

According to one embodiment of this first example according to the invention, at least one of the lateral faces of the said central zone which extends from a short side of the said top is inclined by an angle ranging from −45° to +45° (for example ±30°) with respect to a plane perpendicular to the said top containing the said short side.

This inclination of the or each lateral face of the central zone extending from a short side of the said top contributes to optimize the slippage of the said central zone in the contact area.

According to a further characteristic of this first example, the tread comprises tread-pattern blocks separated from one another by grooves with a width generally equal to or greater than 2 mm, the encircling zone being separated from the central zone by sipes or incision(s) which have a width substantially smaller than that of the said grooves and which are provided to decouple the material of the central zone from that of the encircling zone, each long side of the said top being connected to one of the said tread-pattern elements facing it by one of the said sipes and at least one of the short sides of the said top being connected to the tread-pattern element facing it by one of the said incision(s).

As indicated above, these sipes and/or incision(s) have typically widths less than 2 mm and preferably less than 1 mm. Still more preferably, they have widths ranging from 0.3 mm to 0.8 mm.

It will be noted that the incision which connects the or each short side of the top of the central zone to the corresponding tread-pattern element of the encircling zone has the effect of optimizing the "flattening" of the measuring unit comprising this central zone in the area of contact with the rolling ground.

According to a second exemplary embodiment of the invention which may comprise any one of the characteristics mentioned above in the description of the first example, the said central zone is located in the shoulder zone of the tire and the said condition b) is satisfied by the said inequality (ii).

According to another characteristic of this second example, the said central zone has an elongated shape (for example rectangular or ellipsoid) in the axial direction of the tire.

As indicated above, it will again be noted that this smaller width of the central zone (here in the circumferential direction of the tire) contributes to minimize the "vertical" rigidity Rzz of the central zone and, consequently, to maximize specifically the ratio of rigidities $Ryz_c/Rzz_c$, and hence achieve the desired optimization of the development of slippage of the central zone.

According to a further feature of this second example, the central zone, of parallelepipedal shape, is lodged between the limbs of a first tread-pattern element of the encircling zone with a substantially U-shaped section in a plane perpendicular to the radial direction of the tire, the said limbs extending parallel to the said axial direction and having their respective ends practically aligned with one of the short sides of the said top of the central zone, which short side faces a second parallelepipedal tread-pattern element of the encircling zone.

According to one embodiment of this second example according to the invention, at least one of the lateral faces of the said central zone which extends from a short side of the said top is inclined by an angle ranging from −45° to +45° (for example ±30°) with respect to a plane perpendicular to the said top containing the said short side.

This inclination of the or each lateral face of the central zone extending from a short side of the said top contributes to optimize the slippage of the said central zone in the contact area.

According to a further characteristic of this second example, the tread of the tire comprises tread-pattern blocks separated from one another by grooves, the encircling zone being separated from the central zone by sipes or incision(s) which have a substantially smaller width than that of the said grooves and which are provided to decouple the material of the central zone from that of the encircling zone, the other short side of the said top which faces the web of the said first U-shaped tread-pattern element being connected to the latter by a sipe, whereas the said short side which is aligned with the ends of the said limbs is connected to the said second tread-pattern element by an incision.

In the same way as for the said first exemplary embodiment, it will be noted that this incision has the effect of optimizing the "flattening" of the measuring unit comprising this central zone in the area of contact with the rolling ground.

BRIEF DESCRIPTION OF THE DRAWINGS

The aforementioned characteristics of the present invention, as well as others, will be better understood on reading the following description of an exemplary embodiment of the invention, given by way of illustration and without limitation, the said description relating to the attached drawings, in which:

FIG. 1, FIGS. 5 and 6 are respectively sectional views taken on the planes V-V and VI-VI of FIG. 2 of the tread shown in this FIG. 2.

DESCRIPTION OF EXAMPLARY EMBODIMENTS

Figure 1:
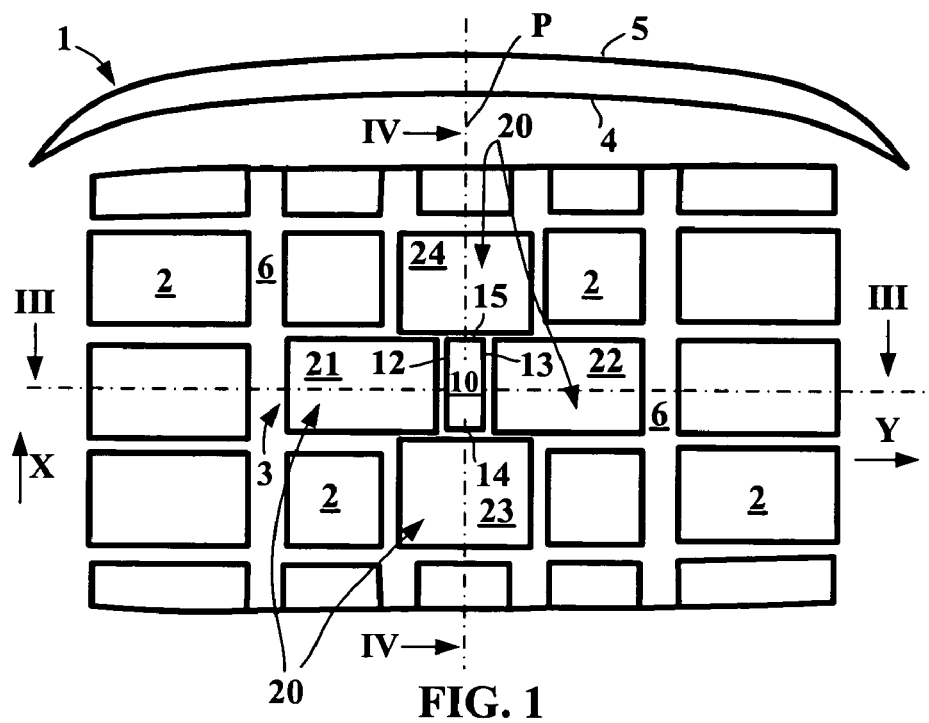
FIG. 1 is a plan view of a sector of a pneumatic tire tread comprising a measuring unit according to a first exemplary embodiment of the invention, with reference to a schematic axial sectional view of this tread.

In FIG. 1 there can be seen a sector of a pneumatic tire tread 1 according to a first exemplary embodiment of the invention, comprising tread-pattern blocks 2, and, below this sector, this tread 1 seen in axial section which has the circumferential mid-plane P of the pneumatic tire as axis of symmetry. It will be noted that the relative dimensions of the various tread-pattern blocks 2 are observed in this FIG. 1. The tread 1 comprises a measuring unit 3 which extends locally from the radially inner face 4 to the radially outer face 5 of this tread 1. In the example of FIG. 1, this measuring unit 3 is centered on the said circumferential mid-plane P.

In the present description, "block" is taken to mean a tread-pattern element 2 with or without a parallelepipedal shape, such as a rubber "bar", which is surrounded over its periphery by a channel or groove 6 connecting it to other blocks. This groove is relatively deep and has a width typically equal to or greater than 2 mm. The measuring unit 3 of FIG. 1 forms a cross substantially with a "+" shape.

This measuring unit 3 comprises a central zone 10 and an encircling zone 20 with the same height in the radial direction Z of the pneumatic tire (see FIGS. 3 and 4), the encircling zone 20 surrounding the central zone 10 and being connected to the latter by sipes and/or incision(s) 30, 31, 32, 33 with a smaller width than that of a groove as mentioned above. These sipes and/or incision(s) 30 to 33, which can be seen in FIGS. 3 and 4 and which have typically widths less than 2 mm and preferably less than 1 mm, are intended to ensure mechanical decoupling of the materials of the central zone 10 and of the encircling zone 20 for the grip measurements.

In this example, the central zone 10 has the shape of a parallelepiped whose rectangular top 11 (i.e. the radially outer face) has its sides 12, 13, 14, 15 respectively facing four tread-pattern elements 21, 22, 23, 24, likewise of parallelepipedal shape, which form the encircling zone 20.

Figure 3:
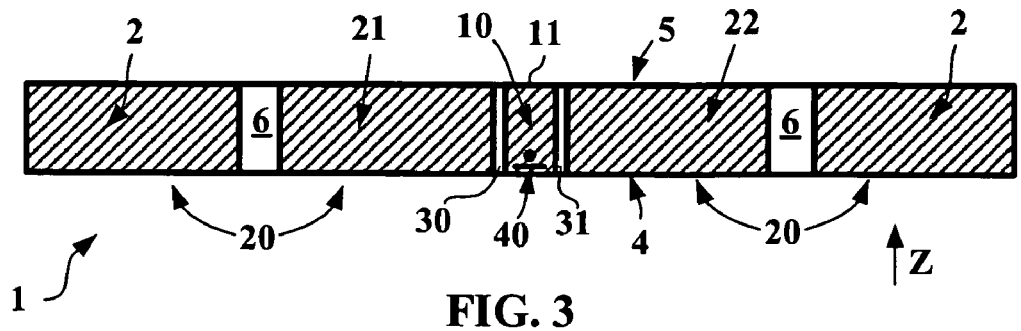
FIGS. 3 and 4 are respectively sectional views taken on the planes III-III and IV-IV of FIG. 1 of the tread shown in this
Figure 4:
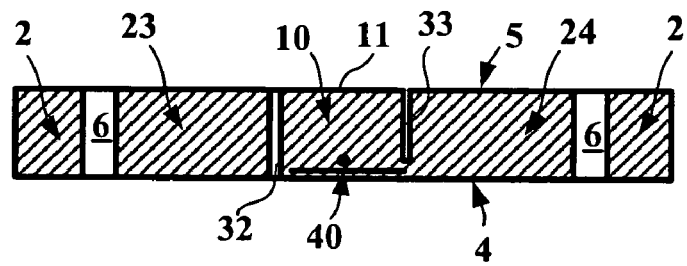

Shown in FIGS. 3 and 4 is a sensor 40 which is sensitive to at least a tangential force exerted on the said top 11 and can measure stresses or displacements. The sensor 40 is lodged within the mass of the central zone 10, radially outside the inner face 4 of the tread 1 and close to this inner face 4, so that this sensor 40 is not affected by the wear of the tread 1 on rolling. A state or states related to the deformations or stresses to which the pneumatic tire is subjected during rolling, at the contact surface facing this place, in the longitudinal and transverse directions is or are to be measured.

This sensor 40 may be for example of the Hall effect type, comprising in a known manner a magnetic element and at least one Hall effect device.

Advantageously, this sensor 40 is a nail-type force sensor as described in European patent application EP-A-1 275 949 in the name of the applicant, the content of which is incorporated in the present description by reference.

In summary, this nail-type sensor is a force sensor comprising a rigid shank intended to be acted upon by a force, and a head, the said head comprising an element attached to the shank and intended to be deformed or stressed when the said shank is acted upon, the said element bearing means for measuring the deformation or stress and comprising anchoring points which have a position relative to the said shank at rest and which substantially maintain this position when the said shank is acted upon, the said anchoring points being discrete or else continuous along the edge of the said deformable element. The said deformable element may be a full membrane, such as a circular membrane, and the said deformable element comprises for example radiating arms connected to one another in a central part where the said shank is fixed, the said anchoring points being situated at the ends of the said arms.

As can be seen in FIGS. 1 and 3, each long side 12, 13 of the said top 11 is connected to the tread-pattern element 21, 22 facing it by a sipe 30, 31 with a width for example equal to 0.8 mm.

As can be seen in FIGS. 1 and 4, one of the short sides 14 of the said top 11 is connected to the tread-pattern element 23 facing it by another sipe 32 with a width similar to those of the sipes 30, 31, whereas the other short side 15 of the said top 11 is connected to the tread-pattern element 24 facing it by an incision 33, the width of which is less than that of the sipes 30 to 32 (the width of the incision 33 may for example range from 0.3 to 0.8 mm). The incision 33 is such that it does not reach the radially inner face 4 of the tread 1, so that it does not totally separate the central zone 10 and the tread-pattern element 24.

As can be seen in the example of FIG. 1, one of the members of the cross formed by the measuring unit 3 comprises in the axial direction Y of the pneumatic tire, on both sides of the central zone 10 and in a manner practically aligned therewith, the two tread-pattern elements 21, 22 facing the long sides 12, 13. As for the other member of this cross which extends in the circumferential direction X of the pneumatic tire, it is such that the two tread-pattern elements 23, 24 facing the short sides 14, 15 have a width greater than that of these latter, so that these elements 23, 24 extend beyond the central zone 10 in the said direction Y.

It will be noted that each sipe 30, 31, 32 helps, upon the passage of the measuring unit 3 through the area of contact with the rolling ground, to reduce the rigidity $Rzz_c$ of the central zone 10 under a force oriented perpendicularly to the radially outer face 5 of the tread 1 compared with the corresponding rigidity $Rzz_e$ of the encircling zone 20.

It will also be noted that the incision 33 helps, upon passage through the contact area, to increase the rigidity $Rxz_c$ of the central zone 10 under a force oriented tangentially to the said radially outer face 5 in the circumferential direction X of the pneumatic tire compared with the corresponding rigidity $Rxz_e$ of the encircling zone 20.

As a result, the sipes 30 to 32 and the incision 33 help overall to increase the ratio of rigidities $Rxz_c/Rzz_c$ for the central zone 10 compared with the corresponding ratio $Rxz_e/Rzz_e$ for the encircling zone 20.

It will also be noted that the area of the top 11 of the central zone 10 is provided to be much smaller than that of the radially outer face of the tread-pattern elements 21, 22, 23, 24 forming the encircling zone 20, so that when the pneumatic tire according to the invention is rolling, this central zone 10 is surrounded over a significant area by the encircling zone 20 which is by definition much more compact than the central zone 10 (i.e. with a vertical rigidity greater than that of the latter), with the result that the said central zone 10 does not take up all of the forces exerted on the crown reinforcement of the pneumatic tire.

In the exemplary embodiment of FIG. 1, the top 11 of the central zone 10 has a length of 20 mm (in the circumferential direction X), a width of 8 mm (in the axial direction Y) and a height of 8 mm (in the radial direction Z), and the area of the top 11 is less than 10% of the area of the encircling zone 20.

In the following description of a second embodiment of the invention relating to FIG. 2, numerical references increased by 100 are used for elements having an analogous function, if not an identical structure, to that of the aforementioned elements relating to FIG. 1.

Figure 2:
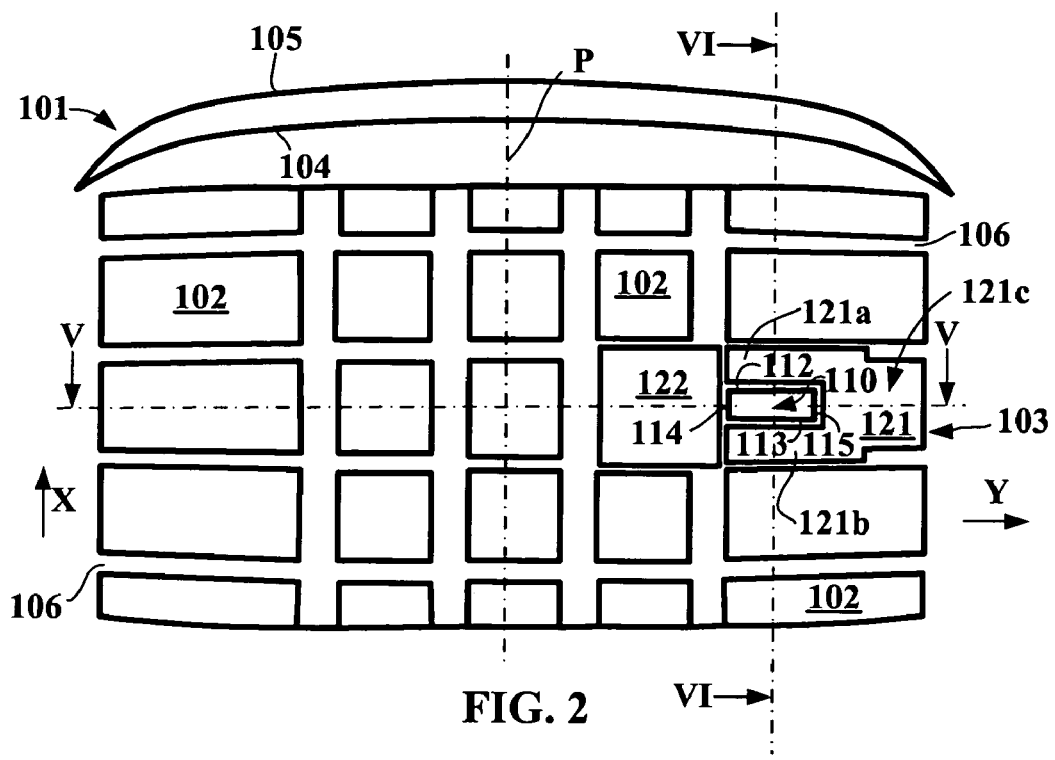
FIG. 2 is a plan view of a sector of a pneumatic tire tread comprising a measuring unit according to a second exemplary embodiment of the invention, again with reference to a schematic axial sectional view of this tread.

In FIG. 2 there can be seen a sector of a pneumatic tire tread 101 according to another exemplary embodiment of the invention, comprising tread-pattern blocks 102, and, below this sector, this tread 101 seen in axial section. The tread 101 comprises a measuring unit 103 which extends locally from the radially inner face 104 to the radially outer face 105 of the tread 101. In the example of FIG. 2, this measuring unit 103 is located in the zone of the pneumatic tire shoulder. It will be noted that the relative dimensions of the various tread-pattern blocks 102 are likewise observed in this FIG. 2.

The measuring unit 103 of FIG. 2 comprises a central zone 110 and an encircling zone 120 with the same height in the radial direction Z of the pneumatic tire (see FIGS. 5 and 6), the encircling zone 120 surrounding the central zone 110 and being connected to the latter by sipes and/or incisions 130, 131, 132, 133 with a smaller width than that of a groove 106 as mentioned above with reference to FIG. 1. As has been mentioned with reference to FIG. 1, the sipes and/or incision(s) 130 to 133, which can be seen in FIGS. 5 and 6 and which have typically widths less than 2 mm and preferably less than 1 mm, are intended to ensure mechanical decoupling of the materials of the central zone 110 and of the encircling zone 120 for the grip measurements.

In this example, the central zone 110 has the shape of a parallelepiped which is elongated in the axial direction Y of the pneumatic tire and which is lodged between the limbs 121a and 121b of a tread-pattern element 121, which forms a part of the encircling zone 120 and has a practically U-shaped section perpendicular to the radial direction Z of the pneumatic tire. More precisely, the limbs 121a and 121b of the element 121 extend parallel to this direction Y and have their respective ends aligned with one of the short sides 114 of the rectangular top 111 of the central zone 110.

Figure 5:
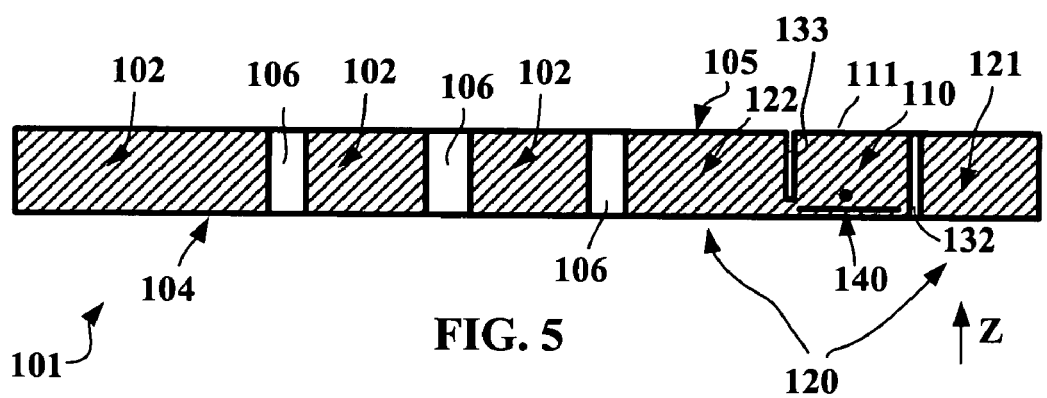
Figure 6:
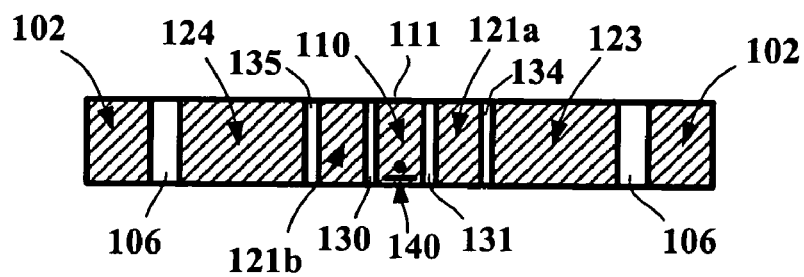

Shown in FIGS. 5 and 6 is a sensor 140, for example of the Hall effect type comprising a magnetic element and at least one Hall effect device, this sensor 140 being sensitive to at least a tangential force exerted on the said top 111 and being able to measure stresses or displacements, in exactly the same way as the sensor 40 described above with reference to FIGS. 3 and 4.

As can be seen in FIGS. 2 and 5, the other short side 115 of the top 111, facing the web 121c of the "U" of the tread-pattern element 121, is connected to the latter by a sipe 132 with a width similar to that of the aforementioned sipe 32, whereas the said short side 114 of the top 111 is connected to another parallelepipedal tread-pattern element 122 likewise forming part of the encircling zone 120 by an incision 133 analogous to the aforementioned incision 33. The incision 133 is thus such that it does not reach the radially inner face 104 of the tread 101, so that it does not totally separate the central zone 110 and the tread-pattern element 122.

As can be seen in FIGS. 2 and 6, each long side 112, 113 of the top 111 is connected to the tread-pattern element 121 by a sipe 130, 131 analogous to the said aforementioned sipes 30 and 31.

It can also be seen that the tread-pattern element 122 extends in the axial direction Y of the pneumatic tire, practically as a continuation of the limbs 121a, 121b of the tread-pattern element 121. Furthermore, two other parallelepipedal tread-pattern elements 123 and 124 complete the encircling zone 120 in such a way that they are respectively connected to the said limbs 121a and 121b of the element 121 by sipes 134 and 135, these elements 123, 124 having a length in the axial direction Y which is practically identical to that of the said element 122.

It will be noted that each sipe 130, 131, 132 helps, upon the passage through the contact area, to reduce the rigidity $Rzz_c$ of the central zone 110 under a force oriented perpendicularly to the radially outer face 105 of the tread 101 compared with the corresponding rigidity $Rzz_e$ of the encircling zone 120.

It will also be noted that the incision 133 helps, upon the passage through the contact area, to increase the rigidity $Ryz_c$ of the central zone 110 under a force oriented tangentially to the said radially outer face 105 in the circumferential direction X of the pneumatic tire compared with the corresponding rigidity $Ryz_e$ of the encircling zone 120.

As a result, the sipes 130 to 132 and the incision 133 helps overall to increase the ratio of rigidities $Ryz_c/Rzz_c$ for the central zone 110 compared with the corresponding ratio $Ryz_e/Rzz_e$ for the encircling zone 120.

It will also be noted that the area of the top 111 of the central zone 110 is provided to be much smaller than that of the radially outer face of the tread-pattern elements 121, 122, 123, 124 forming the encircling zone 120, so that when the pneumatic tire according to the invention is rolling, this central zone 110 is surrounded over a significant area by the encircling zone 120 which is by definition much more compact than the central zone 110 (i.e. with a vertical rigidity greater than that of the latter), with the result that the said central zone 110 does not take up all of the forces exerted on the crown reinforcement of the pneumatic tire.

In the exemplary embodiment of FIG. 1, the top 111 of the central zone 110 has a length of 20 mm (in the axial direction Y), a width of 8 mm (in the circumferential direction X) and a height of 8 mm (in the radial direction Z), and the area of the said top 111 is likewise less than 10% of the area of the encircling zone 120.

Figure 7:
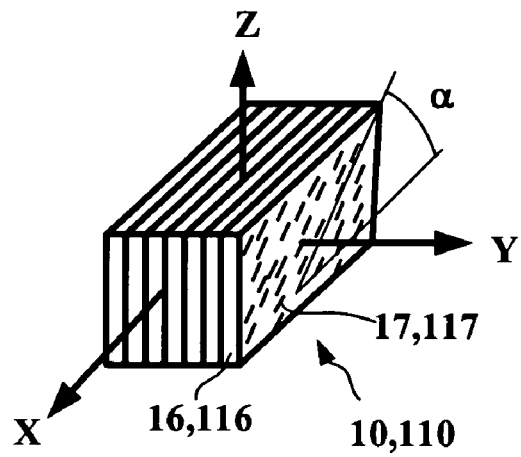
FIG. 7 is a schematic perspective view illustrating the structure of a composite measuring unit according to the invention, comprising reinforcements oriented in the circumferential direction of the pneumatic tire, forming a given angle with this direction.

FIG. 7 illustrates an example of the structure of the central zone 10, 110 of a measuring unit 3, 103 according to the invention.

The central zone 10, 110 of FIG. 7 consists of a parallelepipedal "bar" comprising a plurality of identical rectangular layers 16, 116 which are superposed in the axial direction Y of the pneumatic tire. This "bar" 10, 110 has a composite structure giving it an orthotropic nature owing to the fact that each of the layers 16, 116 is based on the same rubber composition reinforced by textile or metal reinforcements 17, 117.

Tests were carried out on measuring units 3, 103 in which each layer 16, 116 of the central zone 10, 110 is reinforced by textile fibers, for example made of polyester, which are oriented at a given angle±α with respect to the circumferential direction X, in such a way that two adjacent layers 16, 116 respectively comprise these fibers 17, 117 oriented at opposite angles α and −α.

Figure 8:
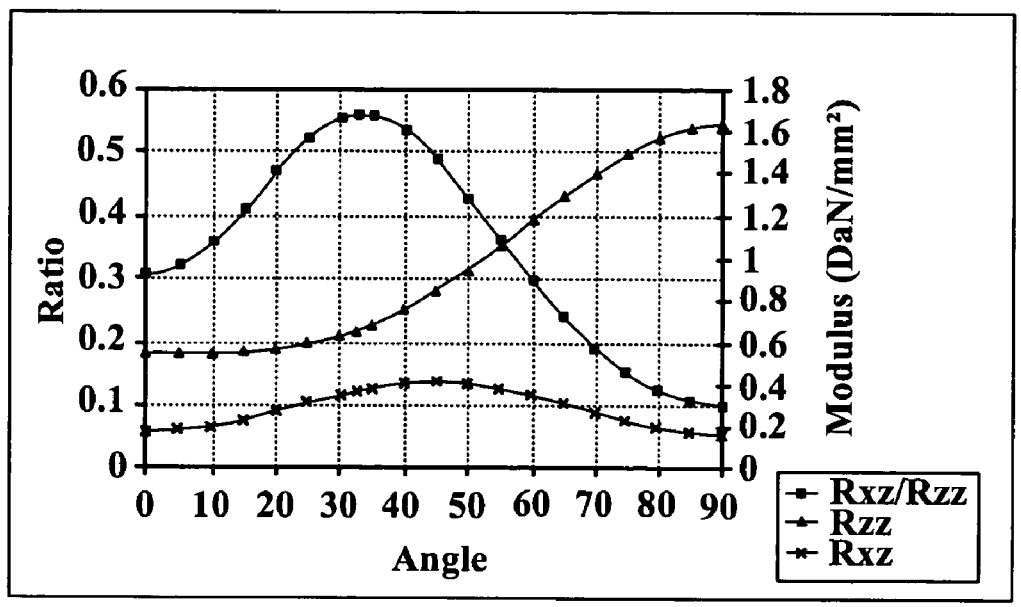
FIG. 8 is a graph illustrating the variation, as a function of the angle of the fibers for a measuring unit according to FIG. 7, on the one hand, of the ratio (rigidity $Rzz_c$ under a force oriented perpendicularly to the surface of the tread/rigidity $Rxz_c$ under a force oriented tangentially to the said surface) and, on the other hand, of the force applied to the said measuring unit.

FIG. 8 shows the results of the tests performed on orthotropic "bars" for the central zone 10, 110 which all comprise eight layers 16, 116, each having a thickness of about 1 mm. These tested "bars" 10, 110 are characterized by an anisotropy equal to 3 and by the arrangement of the fibers at opposite angles±α in two adjacent layers 16, 116.

The variation was measured, as a function of the absolute value α of these angles:
  of the rigidity $Rzz_c$ of the central zone 10, 110 (expressed as $DaN/m^2$) under a force oriented perpendicularly to the radially outer face 5, 105 of the tread 1, 101,
  of the rigidity $Rxz_c$ of the central zone 10, 110 (expressed as $DaN/mm^2$) under a force oriented tangentially to the said radially outer face 5, 105, and
  of the ratio $Rxz_c/Rzz_c$ of these rigidities.

The graph of FIG. 8 shows that a central zone "bar" 10, 110 characterized by angles α practically equal to ±30° alternately in the layers 16, 116 has a ratio of rigidities $Rxz_c/Rzz_c$ which is maximized, thereby helping, in accordance with the invention, to optimize the development of slippage in the contact area of the measuring unit 10, 110 incorporating this "bar" 10, 110.

Furthermore, similar measurements were performed for central zone "bars" 10, 110 having identical dimensions but different structures, in comparison with a "reference" tread-pattern element 21 to 24, 121 to 124 likewise of the "bar" type which is usable in the encircling zone 20, 120.

This "reference" tread-pattern element has a length of 25 mm, a width of 20 mm and a height of 8 mm, and it consists of a crosslinked rubber composition for tread 1, 101. This "reference" tread-pattern element has a rigidity $Rzz_e$ under a force oriented perpendicularly to its radially outer face which is equal to 186 DaN/mm.

A first central zone "bar" 10, 110 according to the invention differs from this "reference" tread-pattern element in that, on the one hand, it consists of a rubber composition having a rigidity $Rzz_c$ under a force oriented perpendicularly to the top 11, 111 of the "bar" 10, 110 which is equal to 17.59 DaN/mm, a value much lower than that of the said "reference" tread-pattern element and, on the other hand, in that it has a width of 5 mm only for a length of 15 mm.

A second central zone "bar" 10, 110 according to the invention differs from the said first "bar" according to the invention in that it consists of a compressible rubber composition in the crosslinked and expanded state, which has a cellular structure with closed cells (i.e. made of "foamed" rubber) giving it a rigidity $Rzz_c$ equal to 11.90 DaN/mm. This second "bar" has, moreover, the same dimensions as the said first "bar" according to the invention.

A third central zone "bar" 10, 110 according to the invention differs from these two "bars" according to the invention in that it has the structure mentioned above with reference to FIG. 7, this structure comprising eight layers 16, 116 with a thickness equal to 1 mm. Each layer 16, 116 comprises a rubber composition which is reinforced by the aforementioned polyester fibers at angles of ±45°, thereby giving this third "bar" a rigidity $Rzz_c$ equal to 17.58 DaN/mm.

For the said "reference" tread-pattern element and these three "bars" 10, 110 according to the invention, the rigidity Rxz under a force oriented tangentially to the radially outer face 5, 105 of the tread 1, 101 was measured, in order to deduce the ratio Rxz/Rzz therefrom. The table below shows the results obtained.

|  | "Reference bar" | First "bar" according to the invention | Second "bar" according to the invention | Third "bar" according to the invention |
|---|---|---|---|---|
| Rxz (DaN/mm) | 22.40 | 3.47 | 3.46 | 5.19 |
| Rzz (DaN/mm) | 186.00 | 17.59 | 11.90 | 17.58 |
| Rxz/Rzz | 0.12 | 0.20 | 0.29 | 0.295 |

These results show in particular that a reduction of the width of the "bar" permits an increase in the ratio Rxz/Rzz (first "bar" according to the invention). The use of a compressible material of the "foamed" rubber type (second "bar" according to the invention) or of a composite material comprising textile fibers (third "bar" according to the invention) likewise permits an increase in this ratio.

The pneumatic tires comprising a tread 1, 101 as described with reference to FIGS. 1 to 7 are such that, in a large range of stresses developed upon contact of the pneumatic tire on the ground during normal operation, a large part, or even the entire central zone 10, 110, of the measuring unit 3, 103 slips on the ground. It has been found that this occurs even on free rolling (no torque) at low speed, including on grounds with strong grip. This slippage phenomenon of the central zone 10, 110 occurs at least during a part of each passage of the measuring unit through the area of contact on the ground. The guarantee of having this slippage phenomenon in the measuring unit 3, 103 makes it possible to measure the friction potential on the ground. In the rest of the tread 1, 101 in contrast, only small parts slip on the ground and these parts which may be subject to slippage are much too small to permit a measurement which can be utilized to arrive at the friction potential.

It has been noted that at the centre of a measuring unit 3, 103 there exists an excellent correlation between the tangentially oriented forces, that is to say those ensuring all the accelerations of the vehicle, including for guiding it, which occur at the contact surface and the parallel forces which can be measured further inside, beyond the limit of the wearing part of the tread 1, 101.

The decoupling ensured by the sipes and incisions 30 to 33 and 130 to 133 makes it possible to carry out the envisaged measurement very acceptably, and it is thought that this is because the central zone 10, 110 satisfies the conditions a) and b) according to the invention which were set out in the preamble of the present description in relation to the encircling zone 20, 120. This makes it possible to avoid the occurrence of ground contact pressures which are too high to permit the slippage of the central zone 10, 110.

An advantage of the invention is to be able in this way to ascertain the available grip margin up to total wear of the pneumatic tire, by means of a measurement of the friction potential performed as indicated above.

The pneumatic tire adapted in this way makes it possible to estimate the "grip potential", a concept defined above and used essentially in connection with the tread 1, 101 as a whole. This pneumatic tire can also make it possible to estimate the "friction potential", a concept likewise defined above.

With one or more appropriate sensors 40, 140, suitably arranged, it is possible to obtain these measurements throughout the service life of the pneumatic tire. It is naturally desirable that the measuring unit 3, 103 is as small as possible compared with the volume of the tread 1, 101, or more fundamentally that this unit 3, 103 does not degrade the performance of the pneumatic tire. The desired information may be obtained by performing a single measurement per revolution of the pneumatic tire. In an advantageous manner, the pneumatic tire may comprise sufficient measuring units 3, 103 to ensure that there is always at least one of them in the area of contact with the ground. As for the vehicle, it is considered to be unnecessary for all of its pneumatic tires to be included in such measurements, one pneumatic tire per side being sufficient.

Based on a pre-established relation for linking the friction potential and the grip potential of the pneumatic tire, on the one hand, and a procedure for regular recalibration using, for example, the property according to which the maximum grip potential of the pneumatic tire under all roadway conditions combined changes little, it is possible to deduce the value of the grip potential of the pneumatic tire from the value of the shear stress exerted on the central zone 10, 110 of a measuring unit 3, 103 or of any signal representative of this shear stress. This recalibration procedure is useful because the pressure beneath the central zone 10, 110 of a measuring unit 3, 103 may change during the use of the pneumatic tire, for example as a function of the wear on the pneumatic tire, for identical conditions of load on the pneumatic tire and of inflation pressure, and this change of the pressure introduces a variable which modifies the relation between the shear stress exerted on the central zone 10, 110 of a measuring unit 3, 103 and the grip potential of the pneumatic tire. If the central zone 10, 110 of a measuring unit 3, 103 is, moreover, equipped to measure the vertical stress at the same point, it is possible to calculate the coefficient of friction between the central zone 10, 110 of a measuring unit 3, 103 and the ground by calculating the ratio between the shear stress and the vertical stress. In this case, it is perhaps not necessary to perform a regular recalibration in order to evaluate the grip potential of the pneumatic tire.

The present invention also extends to a method for detecting a characteristic of grip between an elastic tire and a surface on which the tire rolls (rolling ground), comprising the following steps:

a) providing in the tread at least one measuring unit 3, 103 which is intended to come into contact with the ground on each revolution of the tire, the measuring unit 3, 103 comprising, viewed at a radially outer surface of the tread, a central zone and an encircling zone surrounding the central zone 10, 110, the central zone being adapted to slip on the ground at a level of stresses parallel to the surface of the ground which is substantially lower than the level of stresses parallel to the surface of the ground beyond which the encircling zone 20, 120 slips on the ground;

b) arranging a sensor 40, 140 so as to carry out a measurement in the said central zone, the said sensor 40, 140 being sensitive to at least a parameter reflecting a tangential force exerted at the surface of the said central zone 10, 110;

c) producing a first signal representative of a tangential force in the said contact surface of the said central zone 10, 110;

d) detecting a variation of the said first signal characteristic of a loss of grip;

e) producing an estimate of the friction potential in the said contact surface of the central zone 10, 110;

f) producing an estimate of the grip potential of the tread.

The invention naturally makes it possible to estimate the "available grip margin" from the difference between the grip potential of the elastic tire and the ratio between the tangential force and the vertical force actually applied to the tire. By way of non-limiting illustration, it is possible to estimate the tangential force, for example in the longitudinal direction, as well as the vertical force by means of what is described in U.S. Pat. No. 5,913,240. But it is also possible to estimate the tangential force and the vertical force based on measurements all performed in the tread. Further details on this are given below.

Consequently, in an advantageous variant of the method of detection according to the invention, the steps aimed at detecting a variation of the said first signal and at producing an estimate of the grip potential in the said contact surface of the tire comprise the following operations:

a) producing a second signal representative of a vertical force in the said contact surface of the said central zone;

b) producing from the first and second signals a third signal representative of the ratio between the tangential force and the vertical force;

c) detecting a variation of the said third signal characteristic of a loss of grip;

d) producing an estimate of the friction potential in the said contact surface of the central zone; and e) based on the friction potential, producing an estimate of the grip potential of the said tread.

It is possible to envisage carrying out measurements in the part of the tread external to what is called here "measuring unit", that is to say in the part of the tread whose properties owe nothing to the concern to carry out measurements. In this case, the method proposed by the invention comprises in addition the following steps:

a) arranging a sensor facing a zone of the contact surface of the tread which is external to the measuring unit or units, the said sensor being sensitive to at least a parameter reflecting a tangential force exerted at the surface of the said external zone;

b) producing a first functional tread signal representative of a tangential force in a zone of the contact surface of the tread which is external to the measuring unit or units;

c) producing a second functional tread signal representative of a vertical force in a zone of the contact surface of the tread which is external to the measuring unit or units;

d) producing an indication characteristic of the tangential force applied to the tire, based on the integration of the said first functional tread signal, between the instants of the start and the end of contact with the ground of the said external zone, and over the whole width of the tire;

e) producing an indication characteristic of the vertical force applied to the tire, based on the integration of the said second functional tread signal, between the instants of the start and the end of contact with the ground of the said external zone, and over the whole width of the tire;

f) determining the "available grip margin" from the difference between the grip potential of the tread and the ratio between the said tangential and vertical forces applied to the tread.

Moving on to another aspect of the invention, interesting in itself, it is proposed to estimate the "available grip margin" without going through a measurement or an estimate of the vertical force actually applied to the elastic tire. For this, the invention proposes a method for detecting a characteristic of grip between an elastic tire possessing a deformable tread and a surface on which the tire rolls (rolling ground), comprising the following steps:

a) providing in the tread at least one measuring unit which is intended to come into contact with the ground on each revolution of the tire, the measuring unit comprising, viewed at a radially outer surface of the tread, a central zone and an encircling zone surrounding the central zone, the central zone being adapted to slip on the ground at a level of stresses parallel to the surface of the ground which is substantially lower than the level of stresses parallel to the surface of the ground beyond which the encircling zone slips on the ground;

b) arranging a sensor so as to carry out a measurement in the said central zone, the said sensor being sensitive to at least a parameter reflecting a tangential force exerted at the surface of the said central zone; c) producing a first signal representative of a tangential force in the said central zone;

d) detecting from the said first signal the instant of entry into the contact area of the said central zone;

e) detecting from the said first signal the instant at which the first signal undergoes a variation characteristic of a loss of grip; and f) producing an indication characteristic of an available grip margin based on a function of the first signal between the instant of detection of entry into the contact area and the instant of detection of the said characteristic variation.

The said function of the first signal is advantageously the ratio between the mean value of the first derivative of the said signal with respect to time and the value of the signal at the point characteristic of a loss of grip. As a variant, the said function of the first signal is the time interval separating the said detections.

Finally, as a variant, the invention proposes a method for detecting a characteristic of grip between an elastic tire possessing a deformable tread and a surface on which the tire rolls (rolling ground), comprising the following steps:

a) providing in the tread at least one measuring unit which is intended to come into contact with the ground on each revolution of the tire, the measuring unit comprising, viewed at a radially outer surface of the tread, a central zone and an encircling zone surrounding the central zone, the central zone being adapted to slip on the ground at a level of stresses parallel to the surface of the ground which is substantially lower than the level of stresses parallel to the surface of the ground beyond which the encircling zone slips on the ground;

b) arranging a sensor so as to carry out a measurement in the said central zone, the said sensor being sensitive to at least a parameter reflecting a tangential force exerted at the surface of the said central zone;

c) arranging a sensor opposite a zone of the contact surface of the tread which is external to the measuring unit or units, the said sensor being sensitive to at least a parameter reflecting a tangential force exerted at the surface of the said external zone;

d) producing a first signal representative of a tangential force in the said central zone;

e) producing a second signal representative of a tangential force in the said external zone;

f) producing an indication characteristic of an available grip margin based on a comparison of said first and second signals.

The grip potential of the elastic tire on the roadway directly determines the maximum level of the guiding, braking and driving forces which can be transmitted to the vehicle. It is a critical element in the mobility and road holding of vehicles.

Statistical studies conducted in several countries show that there is an undeniable link between this grip potential and the risk of accidents on a wet roadway: the lower the level of the grip potential on a wet roadway, the higher the risk of an accident. The safety of users therefore depends to a large extent on the grip potential.

An important safety issue is the ability to evaluate the level of the grip potential of the elastic tire as early as possible before it reaches the grip limit, since the possibility of avoiding an accident in the event of insufficient grip will be all the greater as the actions to adapt the rolling conditions of the vehicle are taken at an early stage.

The design principle of the elastic tire presented here represents a considerable advantage from this point of view. It makes it possible, in fact, to evaluate the level of the grip potential even when the tire is rolling freely, which amounts to saying that it is possible to determine this potential under any vehicle rolling conditions, from the situation of rolling in a straight line at constant speed to situations of maximum braking and acceleration, or going around bends at the grip limit. Thus, the available grip potential can be evaluated continuously.

Based on the measurements described, it is also possible to establish what fraction of the grip potential is actually being used.

The following table illustrates applications permitted by a knowledge of this information.

continuously, when the vehicle is rolling, may supply a data base implanted in a computer system connected to the vehicle or external to the vehicle (centralized data base with which the vehicle would communicate); in addition, this information may be compared with the statistical population already stored in the data base in order to determine the percentile of the population to which it corresponds; this result may be converted into a single item of information supplied to the driver (for example, by the indication of an agreed level describing the available grip: high, average, low, very low);

to act on the vehicle:
⇒ by adapting the control strategy of systems of the vehicle such as the wheel-antilock, antiskid and active trajectory monitoring systems: these systems could possess strategies differing according to the grip level and predefined by construction; depending on the instantaneous grip level, the most suitable control strategy could be implemented;
⇒ by permitting the determination of the optimal actions to be applied to a component of the vehicle: numerical simulations in real time can now be performed in the vehicles; with a knowledge of the grip level, it is possible to establish the action to be applied to a component (for example, the brake) in order that the response is optimal; it is also possible to predict by simulation what will be the response of the vehicle to the actions performed by the driver and to consequently correct his actions or to assist him should the actions appear unsuitable;

to inform other road users and bodies responsible for managing the road network, by communicating this information to central data bases; the current means of communication and location of mobile equipment

| INFORMATION GATHERED | RECIPIENT OF THE INFORMATION | | |
|---|---|---|---|
| | DRIVER | VEHICLE | OTHER USERS AND ROAD MANAGERS |
| GRIP POTENTIAL | Inform of the variations of the level of grip potential Compare the instantaneous potential with a statistical population of the grip levels and inform of the position of this instantaneous potential compared with this population (high, average, low, very low level) | Adapt the control strategy of active systems (antilock, antiskid, trajectory monitoring) Assist the driver, correct actions when the latter seem unsuitable or when corrective action seems necessary given the expected response of the vehicle | Inform other users of the available grip level at all points of the network (in combination with a position tracking system) Supply the bodies responsible for the network maintenance with real time data permitting optimum management of the maintenance |
| AVAILABLE GRIP MARGIN | Inform the driver of the level of use of the potential and alert him to the approach of the grip limit | Regulate active systems (antilock, antiskid, trajectory monitoring) | Alert managers of the road networks to points where the grip limit is most often approached |

Based solely on the knowledge of the available grip potential, or of information directly related to the grip potential, it is possible:

to inform the driver of the vehicle:
⇒ when variations of the grip level occur: for example, if the potential declines beyond a certain variation level, an alert may be supplied to the driver in audible or visual form to encourage him to adapt his driving and to increase his vigilance;
⇒ of the relative grip level which is available to him at a given instant compared with a statistical base of the grip levels encountered: the information sampled (GPS system for example) make it possible to assign to each item of information concerning the grip potential supplied by a vehicle, the precise location of the corresponding portion of road, and to transmit this information to a centralized system; on the basis of this information, it is possible:

⇒ to inform other road users and their vehicles of the level available at a given point even before they have reached that point, which makes it possible to anticipate to an even greater extent any corrective actions required at the controls of the vehicles;

⇒to supply the managers of the road network with accurate statistical information in real time on the grip level, thus rendering superfluous the regular operations to measure the grip which are performed in certain countries in order to monitor their road network.

If this information on the available grip potential is complemented with the information on the grip level actually used, it is possible in addition:

- to inform the driver of the rate of use of this available potential and to alert him to the approach of the grip limit;
- to regulate systems of the vehicle (wheel-antilock or antiskid systems, for example) directly from the difference between the available potential and the potential used;
- to supply the persons responsible for managing the road network with statistical information enabling them to detect the points of the network where the grip limit is most often approached and where the risk of an accident may consequently be considerable, even before this risk is highlighted by accident statistics.

It is possible, for example, to carry out a measurement as set out in the patent document DE 3937966 A1. It has been seen that a magnetic element may be incorporated in the central zone of a measuring element, at a place such that this element undergoes a relative displacement with respect to Hall effect sensors placed in the tread when the said measuring element is subjected to a tangential force or to a normal force. The Hall effect sensors are arranged so as to measure the displacement of the magnetic element at least under the effect of a tangential force applied to the surface of a measuring element, or even to measure in addition its displacement, in a clear manner.

As a variant, it would also be possible to carry out a measurement as taught by U.S. Pat. Nos. 5,864,056 or 5,502,433.

The signals thus measured are sent to a calculating unit which determines the grip potential and the available grip margin according to one of the proposed methods. It should be noted that the current technology permits the transmission, preferably the remote transmission, of signals from one or more measuring devices implanted in the tread and the vehicle itself, and that it is not the aim of this invention just to deal with this aspect, which is relatively independent of the measuring aspects which are dealt with here.

These calculated items of information are themselves addressed, for example, to a device enabling the driver to be informed, or else are sent, for example by radio means, to a system external to the vehicle allowing centralization of the information relating to the grip potential of the ground and designed to notify all road users, or else again are used to regulate systems or components of the vehicle to which the elastic tire is fitted.

What is claimed is:

1. An elastic tire with a tread, wherein the tread comprises at least one unit for measuring grip of the tire on a surface on which the tire rolls, the at least one measuring unit being configured to come into contact with the surface on each revolution of the tire, the at least one measuring unit comprising, viewed at a radially outer face of the tread, a central zone and an encircling zone surrounding the central zone, and a sensor sensitive to at least a tangential force exerted on a radially outer top of the central zone, the sensor being provided below the radially outer top of the central zone, the central zone and the encircling zone satisfying conditions of:
   a) $Rzz_c < Rzz_e$, and
   b) (i) $Rxz_c/Rzz_c > Rxz_e/Rzz_e$ or (ii) $Ryz_c/Rzz_c > Ryz_e/Rzz_e$,
   wherein x, y, and z respectively represent circumferential, axial, and radial directions for the tire,
   wherein $Rzz_c$ and $Rzz_e$ respectively represent rigidities of the central zone and the encircling zone under a force oriented perpendicularly to the radially outer face of the tread,
   wherein $Rxz_c$ and $Rxz_e$ respectively represent rigidities of the central zone and the encircling zone under a force oriented tangentially to the radially outer face of the tread in the circumferential direction of the tire, and
   wherein $Ryz_c$ and $Ryz_e$ respectively represent rigidities of the central zone and the encircling zone under a force oriented tangentially to the radially outer face of the tread in the axial direction of the tire and wherein the encircling zone comprises a first tread element separated from the central zone by a sipe and a second tread element separated from the central zone by an incision having a width less than that of the sipe.

2. The elastic tire according to claim 1, wherein the tread further comprises tread-pattern blocks separated from one another by grooves.

3. The elastic tire according to claim 1, wherein an area of the radially outer top of the central zone is less than 20% of an area of a radially outer face of the encircling zone.

4. The elastic tire according to claim 1, wherein the central zone and the encircling zone further satisfy a condition of:
   $Rzz_c < 0.2 Rzz_e$.

5. The elastic tire according to claim 1, wherein the central zone and the encircling zone further satisfy a condition of:
   (i) $Rxz_c/Rzz_c > 1.5\ Rxz_e/Rzz_e$ or (ii) $Ryz_c/Rzz_c > 1.5\ Ryz_e/Rzz_e$.

6. The elastic tire according to claim 1, wherein the central zone has a grip potential that is smaller than that of the encircling zone.

7. The elastic tire according to claim 1, wherein the central zone is formed of a material that includes at least a cellular rubber composition.

8. The elastic tire according to claim 1, wherein the central zone has an orthotropic nature and includes metal or textile reinforcements, and wherein the composite layers are superposed on each other in the axial direction of the tire, if the condition b) (i) is satisfied, or in the circumferential direction of the tire, if the condition b) (ii) is satisfied, the composite layers each being based on a rubber composition in which the metal or textile reinforcements are oriented substantially perpendicularly or parallel to a circumferential mid-plane of the tire.

9. The elastic tire according to claim 8, wherein the composite layers in adjacent pairs respectively include textile fibers, which are oriented at opposite angles (±α) with the circumferential direction or the axial direction of the tire.

10. The elastic tire according to claim 9, wherein the opposite angles (±α) are substantially between ±20° and ±45°.

11. The elastic tire according to claim 1, wherein the central zone substantially has a circumferential mid-plane of the tire as an element of symmetry, and wherein the condition b) (i) is satisfied.

12. The elastic tire according to claim 11, wherein the central zone has an elongated shape in the circumferential direction of the tire.

13. The elastic tire according to claim 12, wherein the central zone, which is of parallelepipedal shape, has its lateral sides respectively facing four parallelepipedal tread-pattern elements forming the encircling zone.

14. The elastic tire according to claim 13, wherein at least one of the lateral sides of the central zone, which extends from a short side of the radially outer top of the central zone, is inclined by an angle ranging from −45° to +45° with respect to a plane perpendicular to the radially outer top of the central zone containing the short side.

15. The elastic tire according to claim 13, wherein the tread further comprises tread-pattern blocks separated from one another by grooves, and, each long side of the radially outer top of the central zone being separated from the encircling zone by the sipe and at least one short side of the radially outer top of the central zone being separated from the encircling zone by the incision.

16. The elastic tire according to claim 1, wherein the central zone is located in a shoulder zone of the tire, and wherein the condition b) (ii) is satisfied.

17. The elastic tire according to claim 16, wherein the central zone has an elongated shape in the axial direction of the tire.

18. The elastic tire according to claim 17, wherein the central zone, which is of parallelepipedal shape, includes at least one lateral face that extends from a short side of the radially outer top of the central zone at an inclined angle ranging from −45° to +45° with respect to a plane perpendicular to the radially outer top of the central zone containing the short side.

19. The elastic tire according to claim 17, wherein the central zone, which is of parallelepipedal shape, is lodged between limbs of the first tread element of the encircling zone with a substantially U-shaped section in a plane perpendicular to the radial direction of the tire, wherein the limbs extend parallel to the axial direction of the tire and have respective ends practically aligned with a short side of the radially outer top of the central zone, the second tread element having a parallelpipedal shape and wherein the short side faces the second parallelpipedal tread element of the encircling zone.

20. The elastic tire according to claim 19, wherein the tread further comprises tread-pattern blocks separated from one another by grooves, wherein the short side of the radially outer top of the central portion is separated from a web portion of the U-shaped section by the sipe, and wherein the short side of the radially outer top of the central portion aligned with the ends of the limbs is separated from the second tread element by the incision.

21. The elastic tire according to claim 1, wherein the sensor, which is sensitive to at least a tangential force, is a force sensor that includes a rigid shank configured to be acted upon by a force and a head, the head including a deformable element attached to the shank and configured to be deformed or stressed when the shank is acted upon, the element bearing means for measuring deformation or stress and including anchoring points, which have a position relative to the shank at rest and which substantially maintain this position when the shank is acted upon, the anchoring points being discrete or else continuous along an edge of the deformable element.

22. The elastic tire according to claim 21, wherein the deformable element is a full membrane.

23. The elastic tire according to claim 22, wherein the deformable element includes radiating arms connected to one another in a central part where the shank is fixed, the anchoring points being situated at respective ends of the arms.

24. A method for detecting a characteristic of grip between an elastic tire and a ground surface on which the tire rolls, the method comprising steps of:
 a) providing in a tread of the tire at least one measuring unit configured to come into contact with the ground surface on each revolution of the tire, the at least one measuring unit including, viewed at a radially outer surface of the tread, an elongate central zone and an encircling zone surrounding the central zone, the central zone being adapted to slip on the ground surface at a stress level substantially lower than a stress level at which the encircling zone slips on the ground surface, wherein stresses causing the central zone to slip are parallel to the ground surface, and wherein the encircling zone comprises a first tread element separated from the central zone by a sipe and a second tread element separated from the central zone by an incision having a width less than that of the sipe;
 b) arranging, in the central zone, a sensor to carry out a measurement in the central zone, the sensor being sensitive to at least a parameter reflecting a tangential force exerted at the contact surface of the central zone;
 c) producing a first signal representative of the tangential force exerted at the contact surface of the central zone;
 d) detecting a variation of the first signal characteristic of a loss of grip;
 e) producing an estimate of a friction potential at the contact surface of the central zone; and
 f) producing an estimate of a grip potential of the tread.

25. The method of claim 24, wherein the steps of detecting a variation of the first signal and producing an estimate of the frictional potential at the contact surface of the central zone includes substeps of:
 producing a second signal representative of a vertical force at the contact surface of the central zone;
 producing from the first and second signals a third signal representative of a ratio between the tangential force and the vertical force;
 detecting a variation of the third signal characteristic of a loss of grip;
 producing the estimate of the friction potential at the contact surface of the central zone based at least in part on the third signal; and
 producing the estimate of the grip potential of the tread based at least in part on the estimated friction potential.

26. The method of claim 24, further comprising steps of:
 arranging a sensor in an external zone of the tread, the external zone being external to the at least one measuring unit and including a contact surface of the tread, the sensor being located below the contact surface of the tread and being sensitive to at least one parameter reflecting a tangential force exerted at the contact surface of the external zone;
 producing a first functional tread signal representative of the tangential force at the contact surface of the external zone;
 producing a second functional tread signal representative of a vertical force at the contact surface of the external zone;
 producing an indication characteristic of the tangential force applied to the tire, based at least in part on an integration of the first functional tread signal, between a start time and an end time of contact of the contact surface of the external zone with the ground surface, and over an entire width of the tire;

producing an indication characteristic of the vertical force applied to the tire, based at least in part on an integration of the second functional tread signal, between the start time and the end time of contact of the contact surface of the external zone with the ground surface, and over the entire width of the tire; and determining an available grip margin from a difference between the grip potential of the tread and a ratio between the tangential and vertical forces applied to the tire.

27. A method for detecting a characteristic of grip between an elastic tire possessing a deformable tread and a ground surface on which the tire rolls, the method comprising steps of:

providing in the tread at least one measuring unit, which is configured to come into contact with the ground surface on each revolution of the tire, the at least one measuring unit including, viewed at a radially outer surface of the tread, an elongate central zone and an encircling zone surrounding the central zone, the central zone being adapted to slip on the ground surface at a stress level substantially lower than a stress level at which the encircling zone slips on the ground surface, wherein stresses causing the central zone to slip are parallel to the ground surface, and wherein the encircling zone comprises a first tread element separated from the central zone by a sipe and a second tread element separated from the central zone by an incision having a width less than that of the sipe;

arranging, in the central zone, a sensor to carry out a measurement in the central zone, the sensor being sensitive to at least a parameter reflecting a tangential force exerted at the contact surface of the central zone;

producing a first signal representative of the tangential force at the contact surface of the central zone;

detecting from the first signal a time of entry into the contact surface of the central zone;

detecting from the first signal a time at which the first signal undergoes a variation characteristic of a loss of grip; and producing an indication characteristic of an available grip margin based at least in part on a function of the first signal between the detected time of entry into the contact surface of the central zone and the detected time of the variation characteristic of a loss of grip.

28. A method for detecting a characteristic of grip between an elastic tire possessing a deformable tread and a ground surface on which the tire rolls, the method comprising steps of:

providing in the tread at least one measuring unit that is configured to come into contact with the ground surface on each revolution of the tire, the at least one measuring unit including, viewed at a radially outer surface of the tread, an elongate central zone and an encircling zone surrounding the central zone, the central zone being adapted to slip on the ground surface at a stress level substantially lower than a stress level at which the encircling zone slips on the ground surface, wherein stresses causing the central zone to slip are parallel to the ground surface, and wherein the encircling zone comprises a first tread element separated from the central zone by a sipe and a second tread element separated from the central zone by an incision having a width less than that of the sipe;

arranging, in the central zone, a first sensor to carry out a measurement in the central zone, the first sensor being sensitive to at least a parameter reflecting a tangential force exerted at the top surface of the central zone;

arranging a second sensor in an external zone of the tread, the external zone having a contact surface and being external to the at least one measuring unit, the second sensor being positioned below the contact surface and being sensitive to at least a parameter reflecting a tangential force exerted at the contact surface of the external zone;

producing a first signal representative of a tangential force exerted at the top surface of the central zone;

producing a second signal representative of a tangential force exerted at the contact surface of the external zone; and producing an indication characteristic of an available grip margin based at least in part on a comparison of said first and second signals.

* * * * *